US00PP31303P3

(12) United States Plant Patent
Berry

(10) Patent No.: US PP31,303 P3
(45) Date of Patent: Dec. 31, 2019

(54) ***HIBISCUS* PLANT NAMED 'JBG 14023'**

(50) Latin Name: *Hibiscus rosa-sinensis*
Varietal Denomination: JBG 14023

(71) Applicant: Capstone Plants, Inc., Grand Saline, TX (US)

(72) Inventor: James Berry, Edgewood, TX (US)

(73) Assignee: Capstone Plants, Inc., Grand Saline, TX (US)

( * ) Notice: Subject to any disclaimer, the term of this patent is extended or adjusted under 35 U.S.C. 154(b) by 0 days.

(21) Appl. No.: 15/998,302

(22) Filed: Aug. 2, 2018

(65) Prior Publication Data

US 2019/0045687 P1 Feb. 7, 2019

Related U.S. Application Data

(60) Provisional application No. 62/605,169, filed on Aug. 3, 2017.

(51) Int. Cl.
*A01H 5/02* (2018.01)
*A01H 6/60* (2018.01)

(52) U.S. Cl.
USPC ..... Plt./257
CPC ..... *A01H 6/608* (2018.05)

(58) Field of Classification Search
USPC ..... Plt./257
CPC ..... A01H 5/02; A01H 6/60; A01H 6/608
See application file for complete search history.

*Primary Examiner* — June Hwu
(74) *Attorney, Agent, or Firm* — The Webb Law Firm

(57) ABSTRACT

A new and distinct *Hibiscus* plant having white colored flowers with light yellow colored highlights that last for several days on the plant over a long flowering season.

1 Drawing Sheet

Botanical classification: *Hibiscus rosa-sinensis.*
Varietal denomination: 'JBG 14023'.

BACKGROUND OF THE INVENTION

The present invention comprises a new and distinct *Hibiscus* plant having the varietal name 'JBG 14023'. The new variety is the result of a planned breeding program with the purposes of developing *Hibiscus rosa-sinensis* plants that exhibit pathogen resistance, multi-day flowers with unique coloration, and possess desirable production traits. 'JBG 14023' is the result of a cross conducted in Grand Saline, Tex. between *Hibiscus rosa-sinensis* varieties 'JBG 12005' (female parent, unpatented) and 'Daisy Mae' (male parent, unpatented). The new variety was selected in December of 2013 in Grand Saline, Tex. and the first asexual reproduction of the new variety was conducted by semi-mature, softwood cuttings in October of 2014 in Grand Saline, Tex. 'JBG 14023' has been trial and field tested and has been found to retain its distinctive characteristics and remain true to type through successive propagations. The present invention has not been evaluated under all possible environmental conditions. The phenotype may vary with variations in environment without a change in the genotype of the plant.

'JBG 14023' is similar to its female parent in having large flowers with overlapping petals with blended colors, but differs from its female parent in having a two-toned and slightly lighter red colored flower center—the flower center of the female parent is solid and reddish black in color. 'JBG 14023' is similar to its male parent in having large flowers and a dark colored throat, but differs from its male parent in exhibiting an increased plant vigor.

When 'JBG 14023' is compared to *Hibiscus rosa-sinensis* variety 'JBG 14020' (unpatented), both varieties exhibit white colored flowers with overlapping petals and a dark colored throat. However, the flowers of 'JBG 14023' have light yellow colored highlights along the side margins that are not present on the flowers of 'JBG 14020'.

The following traits distinguish 'JBG 14023' as a new and distinct cultivar from other *Hibiscus* varieties known to the breeder:

1. White colored flowers with light yellow colored highlights;
2. Overlapping flower petals;
3. Resistance to bacterial leaf spot (*Pseudomonas* spp.); and
4. Multi-day flowers.

DESCRIPTION OF THE DRAWING

The accompanying photographic image illustrates the new variety at approximately one year of age, with the colors being as nearly true as is possible with color illustrations of this type:

FIG. 1 illustrates a close-up view of a flower of the new variety.

DESCRIPTION OF THE PLANT

The following detailed description sets forth the characteristics of the new variety. The color readings and measurements were taken in the summer in Grand Saline, Tex. under natural light on approximately one year old, growing plants in 24.0 cm diameter containers. Color references are primarily to The 1995 R.H.S. Colour Chart of The Royal Horticultural Society of London, 3$^{rd}$ Edition, except where general color terms are used.

PLANT

Time to initiate roots: About 46 days at an average of 24° C.
Time to develop roots: About 51 days at an average of 24° C.
Time to produce a finished flowering plant from a rooted cutting: About 31 weeks in a 24.0 cm diameter container.
Specific disease/pest resistance: Resistance to bacterial leaf spot (*Pseudomonas* spp.).
Heat/cold tolerance: Nothing unusual noted to date; not hardy below 33° F.
Drought tolerance: Nothing unusual noted to date.
Plant:
*Type*.—Tropical, ornamental shrub.
*Habit*.—Upright.
*Height*.—120.0 cm at maturity.
*Spread*.—90.0 cm at maturity.
*Vigor*.—Strong.
Rooting vigor: Strong.
Stem:
*Number per plant*.—15.
*Length*.—Ranging from 29.0-60.5 cm.
*Width*.—5.0 mm-1.0 cm.
*Texture*.—Immature: Smooth. Mature: Vertically ridged.
*Strength*.—High.
*Branch number*.—High; 15.
*Internode length*.—2.0-2.5 cm.
*Color*.—Immature: 144A. Mature: 177B.
*Stipules*.—Number per node: 2. Shape: Linear. Length: 5.0 mm. Width: 1.0 mm. Surface texture: Smooth. Apex: Acute. Base: Linear. Margin: Entire. Color: 144C.
Foliage:
*Arrangement*.—Alternate; simple.
*Size of leaf*.—Length: 6.4 cm. Width: 5.2 cm.
*Shape of leaf* (*generally*).—Ovate, with newer leaves conduplicate — forming a slight cup.
*Shape of apex*.—Acute.
*Shape of base*.—Rounded.
*Texture* (*both surfaces*).—Smooth.
*Margin type*.—Crenate, with a medium amount of incisions beginning halfway up the leaf to the apex.
*Leaf undulation along the margin*.—Absent.
*Color*.—Young leaves: Upper surface: 137C. Lower surface: 138B. Mature leaves: Upper surface: 138A. Lower surface: 138B.
*Veins*.—Venation type: Pinnate. Color: Upper surface: 137B. Lower surface: 138B.
*Petiole*.—Length: 2.5 cm. Diameter: 3.0 mm Texture: Smooth. Color: 143A.

FLOWERS

Buds (described at immaturity):
*Shape*.—Spherical.
*Diameter*.—1.8 cm.
*Length*.—1.2 cm.
*Color*.—143C.
Natural flowering season: From spring through fall in Grand Saline, Tex.
Flower type and habit: Single, with overlapping petals.
Fragrance: None observed.
Flowers (described on the first day of opening):
*Number per stem*.—1.
*Overall depth*.—9.5 cm.
*Overall diameter*.—12.0 cm.
*Shape*.—Rotate; regular.
*Lastingness*.—3 days on the plant.
*Petals*.—Number: 5. Arrangement: Simple. Length: 7.4 cm. Width: Apex: 6.8 cm. Base: 3.9 cm. Shape: Obovate. Apex: Obtuse. Base: Cuneate. Margin: Entire. Undulation: Very weak, slightly ruffled at apical margin. Incisions: Absent. Texture/appearance: Upper surface: Smooth. Lower surface: Smooth. Color (when opening and fully opened): Upper surface: Throat: 60A at 3.0-4.0 cm. Eye: 65A at 1.0-2.0 cm beyond throat. Eye zone extension: Faint and variable 65A — medium to long in length, but thin. Petal color: 155D. Petal apical margin: 4D. Lower surface: Petal apical margin: 4D. Petal color: 155C. Petal distal color: 60A at base of petal — covered by calyx.
*Calyx*.—Form: Fused. Overall length: 2.8 cm. Overall diameter: 3.0 cm. Sepals/calyx lobes: Number: 5. Shape: Ovate. Apex: Acute. Margin: Entire. Color: Outer surface: 139B. Inner surface: 139D.
*Epicalyx*.—Length: 1.0 cm. Width: 3.0 mm Color: 139B.
*Bracts*.—Not present.
*Peduncle*.—Length: 7.3 cm. Diameter: 3.0 mm Strength: Strong. Angle: 30°. Texture: Smooth. Color: 143C.
Reproductive organs:
*Gynoecium*.—Pistils: Number: 1. Length: 7.9 cm. Stigma: Number: 5. Shape: Round. Length: 4.0 mm. Diameter: 3.0 mm. Color: 31A. Style: Length: 6.2 cm. Width: Apex: 2.0 mm. Base: 6.0 mm. Color: 4D. Ovary: Shape: Ovate. Length: 9.0 mm. Width: Apex: 4.0 mm. Base: 6.0 mm. Color: 5D.
*Androecium*.—Stamens: Number: 92. Position: Just below the stigma on the style. Anther: Shape: U-shaped. Diameter: 1.0 mm. Color: 22A. Filament: Length: 6.0 mm. Width: 1.0 mm. Color: 2D. Pollen: Color: 22A.

SEEDS

Seeds:
*Number*.—From 0 to 20.
*Color*.—200C.
*Length*.—5.0 mm.
*Width*.—5.0 mm.

I claim:

1. A new and distinct variety of *Hibiscus* plant, as is herein illustrated and described.

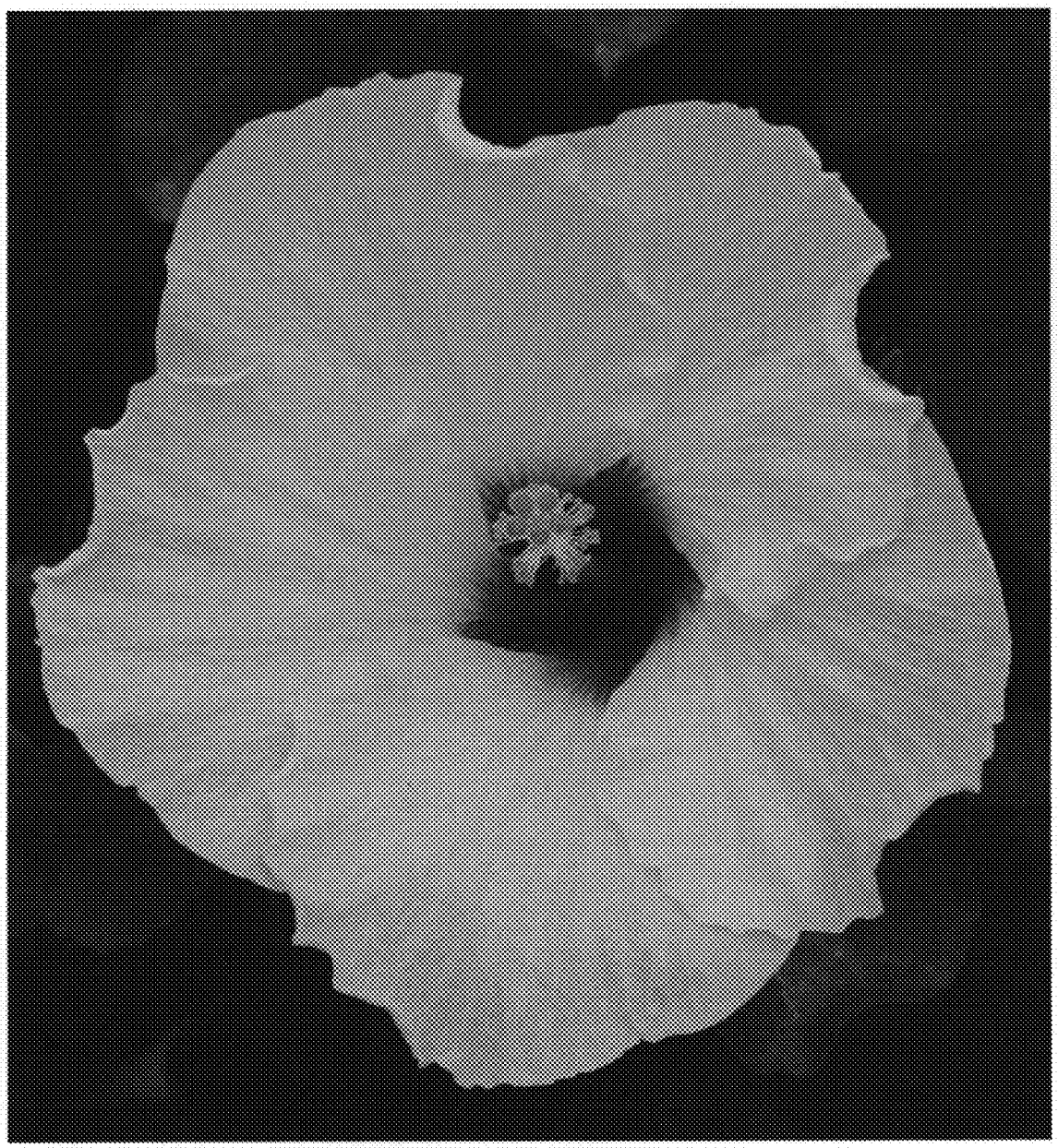

* * * * *